United States Patent [19]
Rausch

[11] 3,992,476
[45] Nov. 16, 1976

[54] PARAFFIN ISOMERIZATON WITH A CATALYTIC COMPOSITE OF PLATINUM OR PALLADIUM METAL, RHODIUM METAL, TIN OXIDE, HALOGEN AND ALUMINA CARRIER

[75] Inventor: Richard E. Rausch, Mundelein, Ill.

[73] Assignee: Universal Oil Products Company, Des Plaines, Ill.

[22] Filed: June 6, 1975

[21] Appl. No.: 584,438

Related U.S. Application Data

[63] Continuation-in-part of Ser. No. 480,793, June 19, 1974, Pat. No. 3,898,154, which is a continuation-in-part of Ser. No. 376,841, July 5, 1973, Pat. No. 3,846,283, which is a continuation-in-part of Ser. No. 201,576, Nov. 23, 1971, Pat. No. 3,745,112, which is a continuation-in-part of Ser. No. 807,910, March 17, 1969, Pat. No. 3,740,328.

[52] U.S. Cl. .......................................... 260/683.68
[51] Int. Cl.² ............................................. C07C 5/30
[58] Field of Search ................... 260/683.68, 683.65

[56] References Cited
UNITED STATES PATENTS

| | | | |
|---|---|---|---|
| 3,557,022 | 1/1971 | Rausch | 260/683.68 |
| 3,558,523 | 1/1971 | Rausch | 260/683.68 |
| 3,642,925 | 2/1972 | Rausch | 260/683.68 |
| 3,709,817 | 1/1973 | Suggitt et al. | 260/683.68 |
| 3,726,810 | 4/1973 | Myers | 260/683.68 |
| 3,879,484 | 4/1975 | Pollitzer | 260/683.65 |
| 3,925,503 | 12/1975 | Parthasarathy | 260/683.65 |
| 3,928,177 | 12/1975 | Hayes | 260/683.68 |

*Primary Examiner*—George Crasanakis
*Attorney, Agent, or Firm*—James R. Hoatson, Jr.; Thomas K. McBride; William H. Page, II

[57] ABSTRACT

Isomerizable hydrocarbons are isomerized using a catalytic composite comprising a combination of a platinum or palladium component, a rhodium component, a tin component and a halogen component with a porous alumina.

11 Claims, No Drawings

PARAFFIN ISOMERIZATON WITH A CATALYTIC COMPOSITE OF PLATINUM OR PALLADIUM METAL, RHODIUM METAL, TIN OXIDE, HALOGEN AND ALUMINA CARRIER

CROSS-REFERENCES TO RELATED APPLICATIONS

This application is a continuation-in-part of my prior copending application Ser. No. 480,792 filed June 19, 1974 and now U.S. Pat. No. 3,898,154, which in turn is a continuation-in-part of my prior application Ser. No. 376,841 filed July 5, 1973 and now U.S. Pat. No. 3,846,283, which in turn is a continuation-in-part of my prior application Ser. No. 201,576 filed Nov. 23, 1971 and now U.S. Pat. No. 3,745,112, and which in turn is a continuation-in-part of my prior application Ser. No. 807,910 filed Mar. 17, 1969 and now U.S. Pat. No. 3,740,328. All of the teachings of these prior applications are specifically incorporated herein by reference.

BACKGROUND OF THE INVENTION

This invention relates to a process for isomerizing isomerizable hydrocarbons including isomerizable paraffins, cycloparaffins, olefins and alkylaromatics. More particularly, this invention relates to a process for isomerizing isomerizable hydrocarbons with a catalytic composite comprising a combination of a platinum or a palladium component, a rhodium component, a tin component and a halogen component with a porous carrier material. The present invention utilizes a dual-function catalytic composite having both a hydrogenation-dehydrogenation function and a cracking function which affords substantial improvements in hydrocarbon isomerization processes that have traditionally used dual-function catalysts.

Processes for the isomerization of hydrocarbons have acquired significant importance within the petrochemical and petroleum refining industry. The demand for para-xylene has created a demand for processes to isomerize other xylene isomers and ethylbenzene to produce para-xylene. The demand for certain branched chain paraffins, such as isobutane or isopentane, as intermediates in producing high octane motor fuel alkylate, can be met by isomerizing the corresponding normal paraffins. It is desired that the alkylate be highly branched to provide a high octane rating. This can be accomplished by alkylating an isoparaffin with $C_3$–$C_7$ internal olefins which, in turn, can be produced by isomerization of corresponding linear alpha-olefins.

Catalytic composites exhibiting a dual hydrogenation-dehydrogenation and cracking function are widely used in the petroleum and petrochemical industry to isomerize hydrocarbons. Such catalysts generally have a heavy metal component, e.g., metals or metallic compounds of Group V through VIII of the Periodic Table, to impart a hydrogenation-dehydrogenation function, with an acid-acting inorganic oxide to impart a cracking function. In catalysis of isomerization reactions, it is important that the catalytic composite not only catalyze the specific desired isomerization reaction by having its dual hydrogenation-dehydrogenation function correctly balanced against its cracking function, but also that the catalyst perform its desired functions well over prolonged periods of time.

The performance of a given catalyst in a hydrocarbon isomerization process is typically measured by the activity, selectivity, and stability of the catalyst. Activity refers to the ability of a catalyst to isomerize the hydrocarbon reactants into the corresponding isomers at a specified set of reaction conditions; selectivity refers to the percent of reactants isomerized to form the desired isomerized product and/or products; stability refers to the rate of change of the selectivity and activity of the catalyst.

The principal cause of instability (i.e., loss of selectivity and activity in an originally selective, active catalyst) is the formation of coke on the catalytic surface of the catalyst during the reaction. This coke is characterizable as a high molecular weight, hydrogen-deficient, carbonaceous material, typically having an atomic carbon to hydrogen ratio of about 1 or more. Thus, a problem in the hydrocarbon isomerization art is the development of more active and selective composites not sensitive to the carbonaceous materials and/or having the ability to suppress the rate of formation of these carbonaceous materials on the catalyst. A primary aim of the art is to develop a hydrocarbon isomerization process utilizing a dual-function catalyst having superior activity, selectivity and stability. In particular, it is desired to provide a process wherein hydrocarbons are isomerized without excess cracking or other decomposition reactions which lower the overall yield of the process and make it more difficult to operate.

SUMMARY OF THE INVENTION

It is an object of this invention to provide a process for isomerizing isomerizable hydrocarbons. It is another object of this invention to provide an isomerization process using a particular isomerization catalyst effective in isomerizing isomerizable hydrocarbons without introducing undesired decomposition and/or cracking reactions. It is a further object of this invention to provide a process for isomerizing isomerizable hydrocarbons utilizing a dual-function catalyst having superior activity, selectivity and stability.

In a broad embodiment, this invention relates to a process for isomerizing an isomerizable hydrocarbon which comprises contacting said hydrocarbon at isomerization conditions with a catalytic composite comprising a porous carrier material containing, on an elemental basis, about 0.01 to about 2 weight percent platinum or palladium, about 0.01 to about 2 weight percent rhodium, about 0.01 to about 5 weight percent tin and about 0.1 to about 10 weight percent halogen, wherein the platinum or palladium, rhodium and tin are uniformly dispersed throughout the porous carrier material, wherein substantially all of the platinum or palladium and rhodium are present in the corresponding elemental metallic states and wherein substantially all of the tin is present in an oxidation state above that of the elemental metal and in a particle size wherein the maximum chord length is less than 100 Angstroms.

In a more specific embodiment, this invention relates to the isomerization of either a saturated or olefinic isomerizable hydrocarbon by contacting the hydrocarbon with the aforementioned catalytic composite at isomerization conditions which include a temperature of about 0° C. to about 450° C., a pressure of about atmospheric to about 100 atmospheres and a liquid hourly space velocity of about 0.1 to about 10. In another limited embodiment this process relates to the isomerization of an isomerizable alkylaromatic hydrocarbon by contacting the alkylaromatic with the aforementioned catalytic composite at isomerization conditions which include a temperature of about 0° C. to about 600° C., a pressure of about atmospheric to about 100 atmospheres, a liquid hourly space velocity of about 0.1 to about 20.0 hr.$^{-1}$ and a hydrogen to hydrocarbon mole ratio of about 1:1 to about 20:1.

Other objects and embodiments referring to alternative isomerizable hydrocarbons and to alternative catalytic compositions will be found in the following further detailed description of this invention.

DESCRIPTION OF PREFERRED EMBODIMENTS

The process of this invention is applicable to the isomerization of isomerizable saturated hydrocarbons including acyclic paraffins and naphthenes and is particularly suitable for the isomerization of straight chain or mildly branched chain paraffins containing 4 or more carbon atoms per molecule such as normal butane, normal pentane, normal hexane, normal heptane, normal octane, etc., and mixtures thereof. Cycloparaffins applicable are those containing at least 5 carbon atoms in the ring such as alkylcyclopentanes and cyclohexanes, including methylcyclopentane, dimethylcyclopentane, cyclohexane, methylcyclohexane, dimethylcyclohexane, etc. This process also applies to the conversion of mixtures of paraffins and/or naphthenes such as those derived by selective fractionation and distillation of straight-run natural gasolines and naphthas. Such mixtures of paraffins and/or naphthenes include the so-called pentane fractions, hexane fractions and mixtures thereof. It is not intended, however, to limit this invention to these enumerated saturated hydrocarbons and it is contemplated that straight or branched chain saturated hydrocarbons and naphthenes containing up to about 20 carbon atoms per molecule may be isomerized according to the process of the present invention with $C_4$–$C_9$ acyclic saturated hydrocarbons and $C_5$–$C_9$ cycloparaffins being particularly preferred.

The olefins applicable within this isomerization process are generally a mixture of olefinic hydrocarbons of approximately the same molecular weight, including the 1-isomer, 2-isomer and other position isomers, capable of undergoing isomerization to an olefin in which the double bond occupies a different position in the hydrocarbon chain. The process of this invention can be used to provide an olefinic feedstock for motor fuel alkylation purposes containing an optimum amount of the more centrally located double bond isomers, by converting the 1-isomer, or other near-terminal-position isomer into olefins wherein the double bond is more centrally located in the carbon atoms chain. The process of this invention is applicable to the isomerization of such isomerizable olefinic hydrocarbons as 1-butene to 2-butene or 3-methyl-1-butene to 2-methyl-2-butene. The process of this invention can be utilized to shift the double bond of an olefinic hydrocarbon such as 1-pentene, 1-hexene, 2-hexene or 4-methyl-1-pentene to a more centrally located position so that 2-pentene, 2-hexene, 3-hexene or 4-methyl-2-pentene, respectively, can be obtained. It is not intended to limit this invention to the enumerated olefinic hydrocarbons. It is contemplated that shifting the double bond to a different position may be effective in straight or branched chain olefinic hydrocarbons containing from 4 up to about 20 carbon atoms per molecule. The process of this invention also applies to the hydroisomerization of olefins wherein olefins are converted to branched-chain paraffins and/or branched olefins.

The process of this invention is also applicable to the isomerization of isomerizable alkylaromatic hydrocarbons, e.g., ortho-xylene, meta-xylene, para-xylene, ethylbenzene, the ethyltoluenes, the trimethylbenzenes, the diethylbenzenes, the triethylbenzenes, normal propylbenzene, isopropylbenzene, etc., and mixtures thereof. Preferred isomerizable alkylaromatic hydrocarbons are the alkylbenzene hydrocarbons, particularly the $C_8$ alkylbenzenes, and non-equilibrium mixtures of various $C_8$ aromatic isomers. Higher molecular weight alkylaromatic hydrocarbons such as the alkylnaphthalenes, the alkylanthracenes, the alkylphenanthrenes, etc., are also suitable.

The isomerizable hydrocarbons may be utilized as found in selective fractions from various naturally-occurring petroleum streams, e.g., as individual components or as certain boiling range fractions obtained by the selective fractionation and distillation of catalytically cracked gas oil. The process of this invention may be utilized for complete conversion of isomerizable hydrocarbons when they are present in minor quantities in various fluid or gaseous streams. The isomerizable hydrocarbons for use in the process of this invention need not be concentrated. For example, isomerizable hydrocarbons appear in minor quantities in various refinery offstreams, usually diluted with gases such as hydrogen, nitrogen, methane, ethane, propane, etc. These offstreams, containing minor quantities of isomerizable hydrocarbons, are obtained from various refinery installations, including thermal cracking units, catalytic cracking units, thermal reforming units, coking units, polymerization units, dehydrogenation units, etc., and have in the past been burned as fuel, since an economical process for the utilization of the hydrocarbon content has not been available. This is particularly true of refinery fluid streams which contain minor quantities of isomerizable hydrocarbons. The process of this invention allows the isomerization of aromatic streams such as reformate to produce xylenes, particularly para-xylene, thus upgrading the reformate from its gasoline value to a high petrochemical value.

As hereinbefore indicated, the catalyst utilized in the process of the present invention comprises a porous carrier material or support having combined therewith catalytically effective amounts of a platinum or palladium component, a rhodium component, a tin component, and a halogen component with a porous carrier material.

Considering first the porous carrier material utilized in the present invention, it is preferred that the material be a porous, adsorptive, high-surface area support having a surface area of about 25 to about 500 m$^2$/g. The porous carrier material should be relatively refractory to the conditions utilized in the isomerization process, and it is intended to include within the scope of the present invention carrier materials which have traditionally been utilized in dual-function hydrocarbon conversion catalysts such as: (1) activated carbon, coke or charcoal; (2) silica or silica gel, silicon carbide, clays and silicates including those synthetically prepared and naturally occurring, which may or may not be acid treated, for example, attapulgus clay, china clay, diatomaceous earth, fuller's earth, kaolin, kieselguhr, etc.; (3) ceramics, porcelain, crushed firebrick, bauxite; (4) refractory inorganic oxides such as alumina, titanium dioxide, zirconium dioxide, chromium oxie, beryllium oxide, vanadium oxide, cesium oxide, hafnium oxide, zinc oxide, magnesia, boria, thoria, silica-alumina, silica-magnesia, chromia-alumina, alumina-boria, silica-zirconia, etc.; (5) crystalline zeolitic alumino-silicates such as naturally occurring or synthetically prepared mordenite and/or faujasite, either in the hydrogen form or in a form which has been treated with multivalent cations; (6) spinels such as $MgAl_2O_4$, $FeAl_2O_4$, $ZnAl_2O_4$, $MnAl_2O_4$, $CaAl_2O_4$ and other like compounds having the formula $MO·Al_2O_3$, where M is a metal having a valence of 2; and (7) combinations of elements from one or more of these groups. The preferred porous carrier materials for use in the present invention are refractory inorganic oxides, with best results obtained with an alumina carrier material. Suitable alumina materials are the crystalline aluminas known as gamma-, eta- and theta-alumina, with gamma- or eta-alumina giving best results. In addition, in some embodiments the alumina carrier material may contain minor proportions of other well known refractory inorganic oxides such as silica, zirconia, magnesia, etc.; however, the preferred support is substantially pure gamma- or eta-alumina. Preferred carrier materials have an apparent bulk density of about 0.3 to about 0.7 g/cc and surface area characteristics such that the average pore diameter is about 20 to 300 Angstroms, the pore volume is about 0.1 to about 1 cc/g and the surface area is about 100 to about 500 $m^2/g$. In general, best results are typically obtained with a gamma-alumina carrier material which is used in the form of spherical particles having: a relatively small diameter (i.e., typically about 1/16 inch), an apparent bulk density of about 0.3 to about 0.8 g/cc., a pore volume of about 0.4 ml/g and a surface area of about 200 $m^2/g$.

The preferred alumina carrier material may be prepared in any suitable manner and may be synthetically prepared or natural occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide, to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, tablets, etc., and utilized in any desired size. For the purpose of the present invention a particularly preferred form of alumina is the sphere; and alumina spheres may be continuously manufactured by the well known oil drop method which comprises: forming an alumina hydrosol by any of the techniques taught in the art and preferably by reacting aluminum metal with hydrochloric acid, combining the resultant hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° F. to about 400° F. and subjected to a calcination procedure at a temperature of about 850° F. to about 1300° F. for a period of about 1 to about 20 hours. This treatment effects conversion of the alumina hydrogel to the corresponding crystalline gamma-alumina. See the teachings of U.S. Pat. No. 2,620,314 for additional details.

One essential constituent of the improved trimetallic composite used in the present invention is a tin component, and it is an essential feature of the present invention that substantially all of the tin component in the composite is in an oxidation state above that of the elemental metal. That is, it is believed that best results are obtained when substantially all of the tin component exists in the catalytic composite in the +2 or +4 oxidation state. Accordingly, the tin component will be present in the composite as a chemical compound such as the oxide, sulfide, halide, oxyhalide, oxysulfide and the like, wherein the tin moiety is in a positive oxidation state, or in chemical combination with the carrier material in a manner such that the tin component is in a positive oxidation state. Controlled reduction experiments with the catalytic composites produced by the preferred methods of preparing the instant catalytic composite have established that the tin component in these catalysts is in a positive oxidation state and is not reduced by contact with hydrogen at temperatures in the range of 1000° to 1200° F. It is important to note that this limitation on the oxidation state of the tin component requires extreme care in preparation and use of the present catalyst to insure that it is not subjected to a reducing atmosphere at temperatures above 1200° F. Equally significant is my observation that it is only when the tin component is in a uniformly dispersed state in the carrier material that it has the capability to maintain its positive oxidation state when subjected to hereinafter described prereduction step. Stated another way, if the tin component is not properly dispersed on the support it can be reduced in the prereduction step and result in an inferior catalyst. Based on the evidence currently available it is believed that best results are obtained when the tin component is present in the catalyst as tin oxide. The term "tin oxide" as used herein refers to a coordinated tin-oxygen complex which is not necessarily stoichiometric.

Interrelated with this oxidation state limitation are the factors of dispersion of the tin component in the support and of particle size of the tin component. This interrelationship emanates from my observation that it is only when the tin component is uniformly dispersed throughout the carrier material in a particle having a maximum chord length less than 100 Angstroms that it can successfully maintain its preferred oxidation state when it is subjected to a high temperature prereduction treatment as hereinafter described. Thus it is an essential feature of my invention that the instant multimetallic catalytic composite is prepared in a manner selected to meet the stated particle size and uniform dispersion limitations. By the use of the expression "uniform dispersion of the tin component in the carrier material" it is intended to describe the situation where the concentration of the tin ingredient is approximately the same in any reasonably divisable portion of the carrier material. Similarly, the expression "particles having a maximum chord length less than 100 Angstroms" is intended to denote particles that would pass through a sieve having a 100 Angstrom mesh size if it were possible to make such a sieve.

The tin component may be incorporated into the catalytic composite in any suitable manner known to effectively disperse this component throughout the carrier material in the required particle size. Thus this component may be added to the carrier by coprecipitation or cogellation of a suitable soluble tin salt with the carrier material, by ion-exchange of suitable tin ions with ions contained in the carrier material when the ion exchange sites are uniformly distributed throughout the carrier or controlled impregnation of the carrier material with a suitable soluble tin salt under conditions selected to result in penetration of all sections of the carrier material by the tin component. One preferred method of incorporating the tin component involves corecipitating it during the preparation of the preferred carrier material, alumina. This method typically involves the addition of a suitable soluble tin compound such as stannous or stannic chloride to an alumina hydrosol, mixing these ingredients to obtain a uniform distribution of the tin moiety throughout the sol and then combining the hydrosol with a suitable gelling agent and dropping the resulting mixture into an oil bath etc., as explained in detail hereinbefore. After drying and calcining the resulting gelled carrier material there is obtained an intimate combination of alumina and tin oxide having the required dispersion and particle size. Another preferred method of incorporating the tin component into the catalytic composite involves utilization of a soluble, decomposable compound of tin to impregnate the porous carrier material. In general, the solvent used in this impregnation step is selected on the basis of the capability to dissolve the desired tin compound and to hold the tin moiety in solution until it is evenly distributed throughout the carrier material and is preferably an aqueous, rather strongly acidic solution. Thus the tin component may be added to the carrier material by commingling the latter with an aqueous solution of a suitable tin salt or suitable compound of tin such as stannous bromide, stannous chloride, stannic chloride, stannic chloride pentahydrate, stannic chloride diamine, stannic trichloride bromide, stannic chromate, stannous fluoride, stannic fluoride, stannic iodide, stannic sulfate, stannic tartrate and the like compounds. The acid used in the impregnation solution may be any organic or inorganic acid that is capable of maintaining the pH of the impregnation solution in the range of about $-1$ or less to about 3 and preferably less than 1 during the impregnation step and that does not contaminate the resultant catalyst. Suitable acids are: inorganic acids such as hydrochloric acid, nitric acid and the like; and strongly acidic organic acids such as oxalic acid, malonic acid, citric acid and the like. A particularly preferred impregnation solution comprises stannic or stannous chloride dissolved in a hydrochloric acid solution containing HCL in an amount corresponding to at least about 5 weight percent of the carrier material which is to be impregnated. Another useful impregnation solution is stannous or stannic chloride dissolved in an anhydrous alcohol such as ethanol. In general, the tin component can be incorporated either prior to, simultaneously with, or after the other metallic components are added to the carrier material. However, I have found that excellent results are obtained when the tin component is incorporated simultaneously with the platinum or palladium and rhodium components. In fact, I have determined that a preferred aqueous impregnation solution contains chloroplatinic acid, rhodium trichloride hydrate, a relatively high amount of hydrogen chloride, and stannic or stannous chloride.

Regardless of which tin compound is used in the preferred impregnation step, it is essential that the tin component be uniformly distributed throughout the carrier material. In order to achieve this objective with an aqueous impregnation solution it is necessary to dilute the impregnation solution to a volume which is approximately equal to or substantially in excess of the void volume of the carrier material which is impregnated and to add a relatively strong acid such as hydrochloric acid, nitric acid and the like to the impregnation solution in an amount calculated to maintain the pH of the impregnation solution in a range of about $-1$ or less to about 3, preferably less than 1. It is preferred to use a volume ratio of impregnation solution to carrier material of at least 0.5:1 and preferably about 1:1 to about 10:1 or more. Similarly, it is preferred to use a relatively long contact time during the impregnation step ranging from about ¼ hour up to about ½ hour or more before drying to remove excess solvent in order to insure a high dispersion of the tin component into the carrier material. The carrier material is, likewise, preferably constantly agitated during this preferred impregnation step.

Regarding the amount of the tin component contained in the instant composite, it is preferably sufficient to constitute about 0.01 to about 5 weight percent of the final composite, calculated on an elemental basis, although substantially higher amounts of tin may be utilized in some cases. Best results are typically obtained with about 0.1 to about 1 weight percent tin.

A second essential ingredient of the subject catalyst is the platinum or palladium component. That is, it is intended to cover the use of platinum or palladium or mixtures thereof as a second component of the present composite. It is an essential feature of the present invention that substantially all of this platinum or palladium component exists within the final catalytic composite in the elemental metallic state. Generally, the amount of this component present in the final catalytic composite is small compared to the quantities of the other components combined therewith. In fact, the platinum or palladium component generally will comprise about 0.01 to about 2 weight percent of the final catalytic composite, caluculated on an elemental basis. Excellent results are obtained when the catalyst contains about 0.05 to about 1 weight percent of platinum or palladium metal.

This platinum or palladium component may be incorporated in the catalytic composite in any suitable manner known to result in a relatively uniform distribution of this component in the carrier material such as coprecipitation or cogellation, ion exchange or impregnation. The preferred method of preparing the catalyst involves the utilization of a soluble, decomposable compound of platinum or palladium to impregnate the carrier material in a relatively uniform manner. For example, this component may be added to the support by commingling the latter with an aqueous solution of chloroplatinic or chloropalladic acid. Other water-soluble compounds of platinum or palladium may be employed in impregnation solutions and include ammonium chloroplatinate, bromoplatinic acid, platinum trichloride, platinum tetrachloride hydrate, platinum dichlorocarbonyl dichloride, dinitrodiaminoplatinum, sodium tetranitroplatinate (II), palladium chloride, palladium nitrate, palladium sulfate, diammine paladium (II) hydroxide, tetrammine palladium (II) chloride, etc. The utilization of a platinum or palladium chloride compound, such as chloroplatinic or chloropalladic acid, is preferred since it facilitates the incorporation of both the platinum or palladium component and at least a minor quantity of the halogen component in a single step. Hydrogen chloride or the like acid is also generally added to the impregnation solution in order to further facilitate the incorporation of the halogen component and the uniform distribution of the metallic components throughout the carrier material. In addition, it is generally preferred to impregnate the carrier material after it has been calcined in order to minimize the risk of washing away the valuable platinum or palladium compounds; however, in some cases it may be advantageous to impregnate the carrier material when it is in a gelled state.

Yet another essential ingredient of the present catalytic composite is a rhodium component. It is of fundamental importance that substantially all of the rhodium component exists within the catalytic composite of the present invention in the elemental metallic state and the subsequently described reduction procedure is designed to accomplish this objective. The rhodium component may be utilized in the composite in any amount which is catalytically effective, with the preferred amount being about 0.01 to about 2 weight percent thereof, calculated on an elemental basis. Typically, best results are obtained with about 0.05 to about 1 weight percent rhodium. It is additionally preferred to select the specified amount of rhodium from within this broad weight range as a function of the amount of the platinum or palladium component, on an atomic basis, as is explained hereinafter.

This rhodium component may be incorporated into the catalytic composite in any suitable manner known to those skilled in the catalyst formulation art which results in a relatively uniform distribution of rhodium in the carrier material. In addition, it may be added at any stage of the preparation of the composite — either during preparation of the carrier material or thereafter — and the precise method of incorporation used is not deemed to be critical. However, best results are obtained when the rhodium component is relatively uniformly distributed throughout the carrier material, and the preferred procedures are the ones known to result in a composite having this relatively uniform distribution. One acceptable procedure for incorporating this component into the composite involves cogelling or coprecipitating the rhodium component during the preparation of the preferred carrier material, alumina. This procedure usually comprehends the addition of a soluble, decomposable compound of rhodium such as rhodium trichloride hydrate to the alumina hydrosol before it is gelled. The resulting mixture is then finished by conventional gelling, aging, drying and calcination steps as explained hereinbefore. A preferred way of incorporating this component is an impregnation step wherein the porous carrier material impregnated with a suitable rhodium-containing solution either before, during or after the carrier material is calcined. Preferred impregnation solutions are aqueous solutions of water soluble, decomposable rhodium compounds such as hexamine rhodium chloride, rhodium carbonylchloride, rhodium trichloride hydrate, rhodium nitrate, sodium hexachlororhodate (III), sodium hexanitrorhodate (III), rhodium sulfate and the like compounds. Best results are ordinarily obtained when the impregnation solution is an aqueous solution of rhodium trichloride hydrate or rhodium nitrate. This component can be added to the carrier material either prior to, simultaneously with, or after the other metallic components are combined therewith. Best results are usually achieved when this component is added simultaneously with the other metallic components. In fact, excellent results are obtained, as reported in the examples, with a one step impregnation procedure using an aqueous solution comprising chloroplatinic or chloropalladic acid, rhodium trichloride, hydrochloric acid and stannous or stannic chloride.

It is essential to incorporate a halogen component into the trimetallic catalytic composite of the present invention. Although the precise form of the chemistry of the association of the halogen component with the carrier material is not entirely known, it is customary in the art to refer to the halogen component as being combined with the carrier material, or with the other ingredients of the catalyst in the form of the halide (e.g., as the chloride). This combined halogen may be either fluorine, chlorine, iodine, bromine, or mixtures thereof. Of these, fluorine and particularly chlorine are preferred for the purposes of the present invention. The halogen may be added to the carrier material in any suitable manner, either during preparation of the support or before or after the addition of the other components. For example, the halogen may be added, at any stage of the preparation of the carrier material or to the calcined carrier material, as an aqueous solution of a suitable, decomposable halogen-containing compound such as hydrogen fluoride, hydrogen chloride, hydrogen bromide, ammonium chloride etc. The halogen component or a portion thereof, may be combined with the carrier material during the impregnation of the latter with the platinum or palladium and rhodium components; for example, through the utilization of a mixture of chloroplatinic acid and hydrogen chloride. In another situation, the alumina hydrosol which is typically utilized to form the preferred alumina carrier material may contain halogen and thus contribute at least a portion of the halogen component to the final composite. The halogen will be typically combined with the carrier material in an amount sufficient to result in a final composite that contains about 0.1 to about 10% and preferably about 1 to about 5%, by weight, of halogen, calculated on an elemental basis. It is to be understood that the specified level of halogen component in the instant catalyst can be achieved or maintained during use in the present isomerization process by continuously or periodically adding to the reaction zone a decomposable halogen-containing compound such as an organic chloride (e.g., ethylene dichloride, carbon tetrachloride, t-butyl chloride) in an amount of about 1 to 100 wt. ppm. of the hydrocarbon feed, and preferably about 1 to 10 wt. ppm.

Regarding the preferred amounts of the various metallic components of the subject catalyst, I have found it to be a good practice to specify the amounts of the rhodium component and the tin component as a function of the amount of the platinum or palladium component. On this basis, the amount of the rhodium component is ordinarily selected so that the atomic ratio of rhodium to platinum or palladium metal contained in the composite is about 0.1:1 to about 2:1, with the preferred range being about 0.25:1 to about 1.5:1. Similarly, the amount of tin component is ordinarily selected to produce a composite containing an atomic ratio of tin to platinum or palladium metal of about 0.1:1 to about 3:1, with the preferred range being about 0.5:1 to about 1.5:1.

Another significant parameter for the instant catalyst is the "total metals content" which is defined to be the sum of the platinum or palladium component, the rhodium component and the tin component, calculated on an elemental basis. Good results are ordinarily obtained with the subject catalyst when this parameter is fixed at a value of about 0.15 to about 3 weight percent, with best results ordinarily achieved at a metals loading of about 0.3 to about 2 weight percent.

Regardless of the details of how the components of the catalyst are combined with the porous carrier material, the final catalyst generally will be dried at a temperature of about 200° to about 600° F. for a period of at least about 2 to about 24 hours or more, and finally calcined or oxidized at a temperature of about 700° F. to about 1100° F. in an air or oxygen atmosphere for a period of about 0.5 to about 10 hours in order to convert substantially all of the metallic components substantially to the oxide form. Because a halogen component is utilized in the catalyst, best results are generally obtained when the halogen content of the catalyst is adjusted during the calcination step by including a halogen or a halogen-containing compound such as HCl in the air or oxygen atmosphere utilized. In particular, when the halogen component of the catalyst is chlorine, it is preferred to use a mole ratio of water to hydrogen chloride of about 5:1 to about 100:1 during at least a portion of the calcination step in order to adjust the final chlorine content of the catalyst to a range of about 0.1 to about 10 weight percent.

An optional ingredient for the trimetallic catalyst of the present invention is a Friedel-Crafts metal halide component. Suitable metal halides of the Friedel-Crafts type include aluminum chloride, aluminum bromide, ferric chloride, ferric bromide, zinc chloride and the like compounds, with the aluminum halides and particularly aluminum chloride ordinarily yielding best results. Generally, this optional ingredient can be incorporated into the composite of the present invention by way of the conventional methods for adding metallic halides of this type; however, best results are ordinarily obtained when the metallic halide is sublimed onto the surface of the carrier material according to the preferred method disclosed in U.S. Pat. No. 2,999,074.

In the preferred method, wherein the calcined composite is impregnated with a Friedel-Crafts metal halide component, the presence of chemically combined hydroxyl groups in the refractory inorganic oxide allows a reaction to occur between the Friedel-Crafts metal halide and the hydroxyl group of the carrier material. For example, aluminum chloride reacts with the hydroxyl groups of the preferred alumina carrier material to yield Al—O—AlCl$_2$ active centers which enhance the catalytic behavior of the composite. It is desired that the combined halogen component be present in the calcined composite within the lower end of the 0.1 to 10 weight percent halogen range. This range of combined halogen content substitutes to some degree for the hydroxyl groups which are necessary for reaction of the carrier material with the Friedel-Crafts metal halide component. This prevents to a small extent, reaction between the Friedel-Crafts metal halide and the carrier material. Some halogen must be present, however, in order to insure that the tin component remains in its dispersed oxidation state in the catalyst.

The Friedel-Crafts metal halide may be impregnated onto the calcined composite containing hydroxyl groups by the sublimation of the Friedel-Crafts metal halide onto the calcined composite under conditions such that the sublimed Friedel-Crafts metal halide is combined with the hydroxyl groups of the calcined composite. This reaction is typically accompanied by the elimination of about 0.5 to about 2.0 moles of hydrogen chloride per mole of Friedel-Crafts metal halide reacted with the carrier material. For example, in the case of subliming aluminum chloride, which sublimes at about 184° C., suitable impregnation temperatures range from about 190° C. to about 700° C., with a preferable range being between about 200° C. and about 600° C. The sublimation can be conducted at atmospheric pressure or under increased pressure and in the presence or absence of diluent gases such as hydrogen or light paraffinic hydrocarbons or both. The impregnation of the Friedel-Crafts metal halide may be conducted batch wise, but a preferred method for impregnating the calcined composite is to pass sublimed AlCl$_3$ vapors, in admixture with an inert gas such as hydrogen, through a calcined catalyst bed. This method both continuously deposits and reacts the aluminum chloride and also removes the evolved HCl.

The amount of Friedel-Crafts metal halide combined with the calcined composite may range from about 1 weight percent up to about 100 weight percent of the Friedel-Crafts metal halide-free, calcined composite. The final composite containing the sublimed Friedel-Crafts metal halide is treated to remove the unreacted Friedel-Crafts metal halide by subjecting the composite to a temperature above the sublimation temperature of the Friedel-Crafts metal halide for a time sufficient to remove from the composite any unreacted Friedel-Crafts metal halide. In the case of AlCl$_3$, temperatures of about 400° C. to about 600° C., and times of from about 1 to about 48 hours are sufficient.

It is an essential feature of the present invention that the resultant oxidized catalytic composite is subjected to a substantially water-free and hydrocarbon-free reduction step prior to its use in the conversion of hydrocarbons. This step is designed to selectively reduce the platinum or palladium and rhodium components to the corresponding metals and to insure a uniform and finely divided dispersion of these matallic components throughout the carrier material, while maintaining the tin component in a positive oxidation state. Preferably substantially pure and dry hydrogen (i.e., less than 20 vol. ppm. H$_2$O) is used as the reducing agent in this step. The reducing agent is contacted with the oxidized catalyst at conditions including a temperature of about 800° F. to about 1200° F. and a period of time of about 0.5 to 2 hours to reduce substantially all of the platinum or palladium and rhodium components to their elemental metallic state while maintaining the tin component in an oxidation state above that of the elemental metal. This reducion treatment may be performed in situ as part of a start-up sequence if precautions are taken to predry the plant to a substantially water-free state and if substantially water-free and hydrocarbon-free hydrogen is used.

The resulting reduced catalytic composite may, in some cases, be beneficially subjected to a presulfiding operation designed to incorporate in the catalytic composite from about 0.01 to about 0.5 weight percent sulfur, calculated on an elemental basis. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the selectively reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 50° F. up to about 1100° F. or more. It is generally a good practice to perform this presulfiding step under substantially water-free conditions.

According to the process of the present invention, an isomerizable hydrocarbon charge stock, preferably in admixture with hydrogen, is contacted with a catalyst of the type hereinbefore described in a hydrocarbon isomerization zone. Contacting may be effected using the catalyst in a fixed bed system, a moving bed system, a fluidized bed system, or in a batch type operation. In view of the danger of attrition loss of the valuable catalyst and of operational advantages, it is preferred to use a fixed bed system. In this system, a hydrogen-rich gas and the charge stock are preheated by suitable heating means to the desired reaction temperature and then passed into an isomerization zone containing a fixed bed of the catalyst type previously characterized. The conversion zone may be one or more separate reactors with suitable means therebetween to insure that the desired isomerization temperature is maintained at the entrance to each zone. It is to be noted that the reactants may be contacted with the catalyst bed in either upward, downward, or radial flow fashion, and that the reactants may be in the liquid phase, a mixed liquid-vapor phase, or a vapor phase when contacted with the catalyst, with best results obtained in a vapor phase.

The process of this invention, utilizing the catalyst described above for isomerizing isomerizable olefinic or saturated hydrocarbons, is preferably effected in a continuous down-flow fixed bed system. One preferred method is to pass the hydrocarbons continuously, preferably commingled with about 0.1 to about 10 moles or more of hydrogen per mole of hydrocarbon, to an isomerization reaction zone containing the catalyst, and to maintain the zone at proper isomerization conditions such as a temperature in the range of about 0° to about 425° C. or more and a pressure of about atmospheric to about 100 atmospheres or more. The hydrocarbon is passed over the catalyst at a liquid hourly space velocity (defined as volume of liquid hydrocarbon passed per hour per volume of catalyst) of from about 0.1 to about 10 hr.$^{-1}$ or more. In addition, diluents such as argon, nitrogen, etc., may be present. The isomerized product is continuously withdrawn, separated from the reactor effluent, and recovered by conventional means such as fractional distillation, while the unreacted starting material may be recycled to form a portion of the feed stock.

The process of this invention for isomerizing an isomerizable alkylaromatic hydrocarbon is preferably effected by contacting the alkylaromatic, in a reaction zone containing the hereinbefore described catalyst, with a fixed catalyst bed by passing the hydrocarbon in a down-flow fashion through the bed, while maintaining the zone at proper alkylaromatic isomerization conditions such as a temperature in the range from about 0° C. to about 600° C. or more, and a pressure of atmospheric to about 100 atmospheres or more. The hydrocarbon is passed, preferably, in admixture with hydrogen at a hydrogen to hydrocarbon mole ratio of about 1:1 to about 25:1 or more, and at a liquid hourly hydrocarbon space velocity of about 0.1 to about 20 hr.$^{-1}$ or more. Other inert diluents such as nitrogen, argon, etc., may be present. The isomerized product is continuously withdrawn, separated from the reactor effluent by conventional means including fractional distillation or crystallization, and recovered.

The following working examples are given to illustrate further the preparation of the trimetallic catalytic composite utilized in the process of the present invention and the employment of the catalyst in isomerization of hydrocarbons. It is to be understood that the examples are illustrative rather than restrictive.

EXAMPLE I

This example demonstrates a particularly good method of preparing the preferred catalytic composite utilized in the process of the present invention.

A tin-containing alumina carrier material comprising 1/16 inch spheres is prepared by: forming an aluminum hydroxyl chloride sol by dissolving substantially pure aluminum pellets in a hydrochloric acid solution, adding stannic chloride to the resulting sol in an amount selected to result in a finished catalyst containing 0.5 weight percent tin, adding hexamethylenetetramine to the resulting tin-containing alumina sol, gelling the resulting solution by dropping it into a hot oil bath to form spherical particles of an aluminum hydrogel containing tin in a particle size which is less than 100 Angstroms maximum chord length, aging and washing the resulting particles and finally drying and calcining the aged and washed particles to form spherical particles of gamma-alumina containing about 0.3 weight percent combined chloride and a uniform dispersion of about 0.5 weight percent tin in the form of tin oxide. Additional details as to this method of preparing the preferred carrier material are given in the teachings of U.S. Pat. No. 2,620,314.

An aqueous impregnation solution containing chloroplatinic acid, rhodium chloride hydrate and hydrogen chloride is then prepared. This solution is then intimately admixed with the tin-containing gamma-alumina particles in amounts, respectively, calculated to result in a final composite containing, on an elemental basis, 0.6 weight percent platinum, 0.1 weight percent rhodium and 0.5 weight percent tin. In order to insure uniform distribution of the metallic components throughout the carrier material, the amount of hydrogen chloride corresponds to about 2 weight percent of the alumina particles. This impregnation step is performed by adding the carrier material particles to the impregnation mixture with constant agitation. In addition, the volume of the solution is approximately the same as the void volume of the carrier material particles. The impregnation mixture is maintained in contact with the carrier material particles for a period of about ½ hour at a temperature of about 70° F. Thereafter, the temperature of the impregnation mixture is raised to about 225° F. and the excess solution is evaporated in a period of about 1 hour. The resulting dried particles are then subjected to a calcination treatment in an air atmosphere at a temperature of about 925° F. for about 1 hour. The calcined spheres are then contacted with an air stream containing $H_2O$ and HCl in a mole ratio of about 40:1 for about 2 hours at 975° F. in order to adjust the halogen content of the catalyst particles to a value of about 1.2.

The resulting catalyst particles are analyzed and found to contain, on an elemental basis, about 0.6 weight percent platinum, about 0.1 weight percent rhodium, about 0.5 weight percent tin and about 1.2 weight percent chloride. For this catalyst, the atomic ratio of tin to platinum is 1.37:1 and the atomic ratio of rhodium to platinum is 0.316:1.

Thereafter, the catalyst particles are subjected to a dry prereduction treatment designed to reduce the platinum and rhodium components to the elemental state while maintaining the tin component in a positive oxidation state by contacting them for 1 hour with a substantially pure hydrogen stream containing less than 5 vol. ppm. $H_2O$ at a temperature of about 1050° F., a pressure slightly above atmospheric and a flow rate of the hydrogen stream through the catalyst particles corresponding to a gas hourly space velocity of about 720 $hr.^{-1}$.

EXAMPLE II

A portion of the spherical trimetallic catalyst particles produced by the method described in Example I is loaded into a continuous, fixed bed isomerization plant of conventional design. The charge stock, containing on a weight percent basis, 20.0% ethylbenzene, 10.0% para-xylene, 50.0% meta-xylene, and 20.0% ortho-xylene is commingled with about 8 moles of hydrogen per mole of hydrocarbon, heated to 400° C., and continuously charged at 4.0 $hr.^{-1}$ liquid hourly space velocity (LHSV) to the reactor which is maintained at a pressure of about 400 psig. The resulting product evidences essentially equilibrium conversion to para-xylene with only insignificant amounts of cracked products thus indicating an efficient alkylaromatic isomerization catalyst.

EXAMPLE III

A portion of the catalyst produced by the method of Example I is placed in a continuous flow, fixed bed isomerization plant of conventional design as utilized in Example II. Substantially pure meta-xylene is used as a charge stock. The charge stock is commingled with about 8 moles of hydrogen per mole of hydrocarbon, heated to about 390° C., and continuously charged to the reactor which is maintained at a pressure of about 300 psig. Substantial conversion of meta-xylene to para-xylene is obtained, i.e., greater than 80% of equilibrium.

EXAMPLE IV

A catalyst identical to that produced in Example I but containing only 0.40 weight percent combined chloride is used to isomerize 1-butene in an appropriate isomerization reactor, at a reactor pressure of about 500 psig, and a reactor temperature of about 140° C. Substantial conversion to 2-butene is observed.

EXAMPLE V

The same catalyst as utilized in Example IV is charged to an appropriate, continuous isomerization reactor of conventional design maintained at a reactor pressure of about 1000 psig. and a reactor temperature of about 180° C. 3-methyl-1-butene is continuously passed to this reactor with substantial conversion to 2-methyl-2-butene being observed.

EXAMPLE VI

A catalyst, identical to that catalyst produced in Example I except that the gamma-alumina particles are contacted with hydrogen fluoride to provide a 2.9 weight percent combined fluoride content in the catalyst, is placed in an appropriate continuous isomerization reactor of conventional design maintained at a reactor pressure of about 300 psig. and a reactor temperature of about 200° C. Normal hexane is continuously charged to the reactor and an analysis of the product stream shows substantial conversion of 2,2-dimethylbutane, 2,3-dimethylbutane, 2-methylpentane, and 3-methylpentane.

EXAMPLE VII

A portion of the catalyst prepared in Example I is placed in an appropriate continuous isomerization apparatus and used to isomerize normal butane at a reactor pressure of 300 psig., a 0.5 hydrogen to hydrocarbon mole ratio, a 1.0 liquid hourly space velocity, and a reactor temperature of 230° C. Substantial conversion of normal butane to isobutane is observed, i.e., approximately a conversion of normal butane to isobutane of about 45 weight percent of the original butane charged.

EXAMPLE VIII

A portion of the catalyst prepared in Example I is placed in an appropriate continuous isomerization reactor maintained at a reactor temperature of about 210° C. and a reactor pressure of about 250 psig. Methylcyclopentane is continuously passed to this reactor with a substantial conversion to cyclohexane being observed.

I claim as my invention:
1. A process for isomerizing an acyclic paraffin hydrocarbon which comprises contacting said hydrocarbon at isomerization conditions with a catalytic composite comprising a porous alumina carrier containing, on an elemental basis, about 0.01 to about 2 weight percent platinum or palladium, about 0.01 to about 2 weight percent rhodium, about 0.01 to about 5 weight percent tin and about 0.1 to about 10 weight percent halogen, wherein said platinum or palladium, rhodium and tin are uniformly dispersed throughout said alumina, wherein substantially all of said platinum or palladium and said rhodium are present in the corresponding elemental metallic states and wherein substantially all of said tin is present in an oxidation state above that of the elemental metal.

2. A process as defined in claim 1 wherein said halogen is chlorine.

3. A process as defined in claim 1 wherein the atomic ratio of tin to platinum or palladium contained in said composite is about 0.1:1 to about 3:1.

4. A process as defined in claim 1 wherein the atomic ratio of rhodium to platinum or palladium contained in said composite is about 0.1:1 to about 2:1.

5. A process as defined in claim 1 wherein said catalytic composite contains about 0.01 to about 0.5 weight percent sulfur, calculated on an elemental basis.

6. A process as defined in claim 1 wherein said composite contains about 0.05 to about 1 weight percent platinum, about 0.05 to about 1 weight percent rhodium, about 0.1 to about 1 weight percent tin and about 1 to about 5 weight percent halogen.

7. A process as defined in claim 1 wherein said catalytic composite additionally contains from 1 weight percent up to about 100 weight percent of said composite.

8. A process as defined in claim 7 wherein the Friedel-Crafts metal halide is aluminum chloride.

9. A process as defined in claim 1 wherein said hydrocarbon is a $C_4 - C_{20}$ acyclic paraffin and said isomerization conditions include a temperature of about 0° to about 425° C., a pressure of about atmospheric to about 100 atmospheres and a liquid hourly space velocity of about 0.1 to about 10 hr.$^{-1}$.

10. A process as defined in claim 9 wherein said paraffin hydrocarbon is commingled with about 0.1 to about 10 moles of hydrogen per mole of hydrocarbon prior to said contacting.

11. A process as defined in claim 9 wherein said paraffin hydrocarbon is selected from $C_4$-$C_9$ acyclic paraffins.

* * * * *